United States Patent
Lavoie (12) 
(10) Patent No.: US 6,497,159 B1
(45) Date of Patent: Dec. 24, 2002

(54) BRACELET FOR MOVING ULTRASONIC SENSORS ALONG A PIPE

(75) Inventor: Eric Lavoie, Montréal (CA)

(73) Assignee: Hydro-Quebec, Montreal (CA)

( * ) Notice: Subject to any disclaimer, the term of this patent is extended or adjusted under 35 U.S.C. 154(b) by 116 days.

(21) Appl. No.: 09/592,115

(22) Filed: Jun. 12, 2000

(51) Int. Cl.⁷ .................. G01N 19/00; G01N 29/24; G01N 29/26
(52) U.S. Cl. .................. 73/866.5; 73/661
(58) Field of Search .................. 73/866, 86, 592, 73/638, 622, 661

(56) References Cited

U.S. PATENT DOCUMENTS

| | | |
|---|---|---|
| 3,289,468 A | 12/1966 | Van Der Veer et al. |
| 3,602,036 A | 8/1971 | Peterson et al. |
| 3,921,440 A | 11/1975 | Toth |
| 4,117,733 A | 10/1978 | Gugel .................. 73/634 |
| 4,285,242 A | 8/1981 | Braithwaite .................. 73/623 |
| 4,295,092 A | 10/1981 | Okamura .................. 73/864 |
| 4,307,616 A | 12/1981 | Vasile .................. 73/643 |
| 4,312,230 A | 1/1982 | Bricker et al. .................. 73/638 |
| 4,375,165 A | 3/1983 | De Sterke .................. 73/622 |
| 4,467,654 A | 8/1984 | Murakami et al. .................. 73/640 |
| 4,586,379 A | 5/1986 | Burkhardt, Jr. .................. 73/622 |
| 4,679,437 A | 7/1987 | Koike et al. .................. 73/622 |
| 4,779,453 A | 10/1988 | Hopenfeld .................. 73/86 |
| 4,843,884 A | 7/1989 | House et al. .................. 73/622 |
| 4,922,748 A | 5/1990 | Hopenfeld .................. 73/86 |
| 5,138,644 A | 8/1992 | McArdle et al. .................. 378/55 |
| 5,174,155 A | 12/1992 | Sugimoto .................. 73/622 |
| 5,313,837 A | 5/1994 | Haynes .................. 73/622 |
| 5,359,897 A | 11/1994 | Hamstead et al. .................. 73/597 |
| 5,438,872 A | 8/1995 | Kobayashi et al. .................. 73/597 |
| 5,583,292 A | 12/1996 | Karbach et al. .................. 73/638 |
| 5,585,565 A | 12/1996 | Glascock et al. .................. 73/644 |
| 5,619,423 A | 4/1997 | Scrantz .................. 73/422 X |
| 5,686,675 A | 11/1997 | Barton .................. 73/866.5 |
| 5,756,898 A | 5/1998 | Diatschendo et al. .................. 73/592 |
| 5,770,800 A | 6/1998 | Jenkins et al. .................. 73/623 |
| 5,963,030 A | 10/1999 | Stark .................. 324/229 |
| 5,965,818 A | 10/1999 | Wang .................. 73/598 |
| 6,000,288 A | 12/1999 | Kwun et al. .................. 73/597 |
| 6,003,377 A | 12/1999 | Waag et al. .................. 73/625 |

FOREIGN PATENT DOCUMENTS

| | | | |
|---|---|---|---|
| EP | 0 633 451 | 1/1995 | .......... G01B/17/00 |
| EP | 0 985 905 | 3/2000 | .......... G01B/17/02 |

OTHER PUBLICATIONS

Derwent Acc–No: 1993–262760; RO 104404 A Inventor Otlacan et al; "Manometer With External Fixing on Pipe–Log Circular Blade Attached Like Bracelet on Pipe and Supporters Several Stress Transducers Which Sense Pipe Dimension Variation", Jul. 1992.*

* cited by examiner

Primary Examiner—Thomas P. Noland
(74) Attorney, Agent, or Firm—Foley & Lardner (57) ABSTRACT

A bracelet for moving sensors along a straight or elbow pipe. The bracelet has a number of side-by-side positionable supports for removably holding the sensors respectively. A flexible attachment is provided for holding the supports in a pliant side-by-side series arrangement. The attachment has opposite ends extending beyond the supports at opposite ends of the series arrangement. The bracelet further has a frame having an inner circular opened surface for installation around the pipe, and a longitudinal circular side receiving surface along which the series arrangement of the supports is mounted. The side receiving surface is provided with fastening members projecting at both ends of the series arrangement of the supports. The ends of the attachment is supported by the fastening members.

43 Claims, 7 Drawing Sheets

BRACELET FOR MOVING ULTRASONIC SENSORS ALONG A PIPE

FIELD OF THE INVENTION

The present invention relates to a bracelet for moving sensors along a straight or elbow pipe, as used for measuring the thickness or another physical feature of the pipe with ultrasonic or other types of sensors.

BACKGROUND OF THE INVENTION

Water pipes used in nuclear reactors are subject to long-term water flow corrosion and erosion problems, also known as "Flow Assisted Corrosion". These problems lead to thinning of the pipes and ultimately to their bursting. Regular preventive inspections must therefore be carried out in order to detect any thinning in the pipes. The bent sections of the pipes are especially vulnerable to this type of corrosion, but are difficult to inspect. Also, pipes in nuclear reactors are hard to reach in cramped locations.

Known devices used to measure thickness of these pipes are ill-equipped to provide accurate readings. Furthermore, these are cumbersome and difficult to operate.

Known in the art, there is the bracelet used by the Specialized Inspection and Maintenance Department "SIMD" of Hydro Ontario. The "SIMD" bracelet has a mid grasping portion and side pivoting legs attached to the mid grasping portion. The side pivoting legs contain supports housing only a few ultrasonic sensors. An encoder is mounted in the center of the mid grasping part. Small magnets are used to maintain the supports in contact with the surface of a pipe. A curved flexible rod is attached at side edges of the pivoting legs to maintain these in an open biased position.

To use the "SIMD" bracelet, a user has to manually force the legs against a pipe to be inspected. The inspection of the pipe is done in three (3) distinct passes, which are spaced-apart by about 30° each since the bracelet discontinously covers less than half the pipe's circumference. The passes are then combined by a software program, which provides an image of the inspected pipe. The "SIMD" bracelet requires great dexterity from the operator to ensure that all three (3) passes are perfectly aligned.

Known in the art are U.S. Pat. No. 5,174,155 (SUGIMOTO); U.S. Pat. No. 4,375,165 (DE STERKE); U.S. Pat. No. 3,602,036 (PETERSON); U.S. Pat. No. 3,921,440 (TOTH); U.S. Pat. No. 5,585,565 (GLASCOCK, et al.); U.S. Pat. No. 5,619,423 (SCRANTZ); U.S. Pat. No. 5,583,292 (KARBACH et al.); U.S. Pat. No. 6,003,377 (WAAG et al.); U.S. Pat. No. 5,963,030 (STARK); U.S. Pat. No. 4,586,379 (BURCKHARDT, Jr.); U.S. Pat. No. 4,467,654 (MURAKAMI et al.); U.S. Pat. No. 5,359,897 (HAMSTEAD et al.); U.S. Pat. No. 5,313,837 (HAYNES); U.S. Pat. No. 4,307,616 (VASILE); U.S. Pat. No. 5,438,872 (KOBAYASHI et al.); U.S. Pat. No. 4,679,437 (KOIKE et al.); U.S. Pat. No. 4,312,230 (BRICKER et al.); U.S. Pat. No. 5,756,898 (DIATSCHENKO et al.); U.S. Pat. No. 6,000,288 (KWUN et al.); U.S. Pat. No. 4,285,242 (BRAITHWAITE); U.S. Pat. No. 4,117,733 (GUGEL); U.S. Pat. No. 5,770,800 (JENKINS et al.); U.S. Pat. No. 4,295,092 (OKAMURA); U.S. Pat. No. 5,138,644 (McARDLE et al.); U.S. Pat. No. 5,965,818 (WANG); U.S. Pat. No. 4,922,748 (HOPENFELD); and U.S. Pat. No. 4,779,453 (HOPENFELD), which show various devices for pipe inspection, but are all poorly or simply not adequate for inspecting the thickness of a pipe with elbow sections.

SUMMARY OF THE INVENTION

An object of the present invention is to provide a bracelet for moving sensors along a pipe, as used for measuring the thickness or another physical feature of the pipe, and which is adapted to bent or elbow pipes and is easy to use even in cramped spaces and does not suffer from the drawbacks of the prior art.

Another object of the invention is to provide such a bracelet, which allows for a coherent and continuous inspection of a pipe having elbow sections or not.

Another object of the invention is to provide such a bracelet, which can maintain the spacing between the ultrasonic sensors while following the surface to be inspected for good contact between the sensors and the pipe.

According to the present invention, there is provided a bracelet for moving sensors along a pipe, comprising:

a number of side-by-side positionable supports for removably holding the sensors respectively;

a flexible attachment for holding the supports in a pliant side-by-side series arrangement, the attachment having opposite ends extending beyond the supports at opposite ends of the series arrangement; and a frame having an inner circular opened surface for installation around the pipe, and a longitudinal circular side receiving surface along which the series arrangement of the supports is mounted, the side receiving surface being provided a with fastening members projecting at both ends of the series arrangement of the supports, the ends of the attachment being supported by the fastening members.

Preferably, when the sensors are ultrasonic sensors, each support has a coupling liquid channel with a bottom opening extending under the sensor held by the support.

Preferably, the flexible attachment is fastened to the frame by means of an elastic strap extending over the supports and urging them against the pipe for better contact therewith.

With the above bracelet, pipes with elbow sections can be inspected in a single continous pass, with a minimum of training required from the operator/user, and without dismantling the pipe.

BRIEF DESCRIPTION OF THE DRAWINGS

The invention as well as its numerous advantages will be better understood by the following non restrictive description of preferred embodiments made in reference to the appending drawings in which.

DESCRIPTION OF PREFERRED EMBODIMENTS

Figure 13:
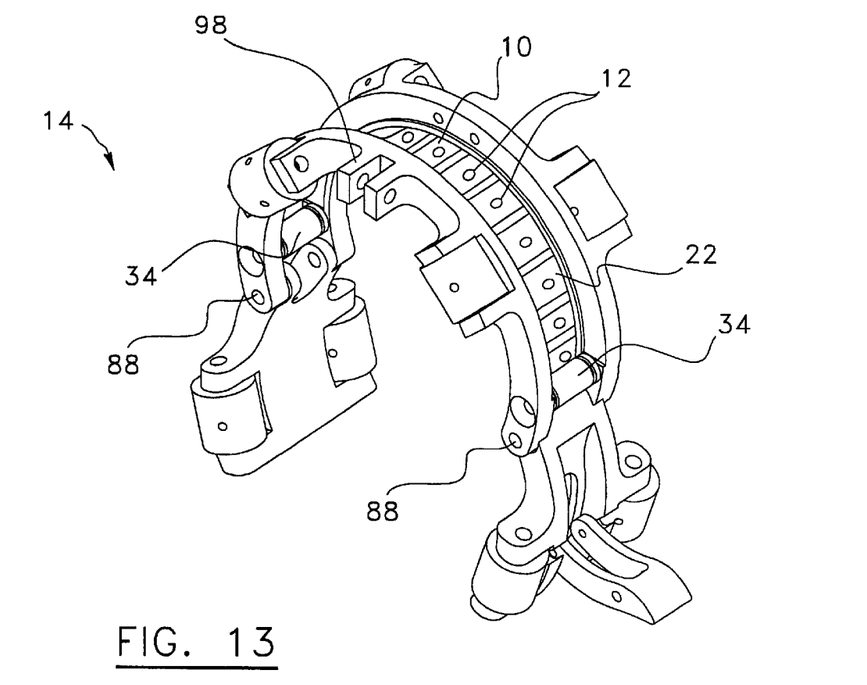
FIG. 13 is a perspective view of an open bracelet, according to the present invention.

Referring to FIG. 13, there is shown a bracelet 14 for moving ultrasonic sensors 12 along a pipe (not shown), according to the present invention. The bracelet 14 comprises a number of side-by-side positionable supports 10 for removably holding the sensors 12 respectively.

Figure 2:
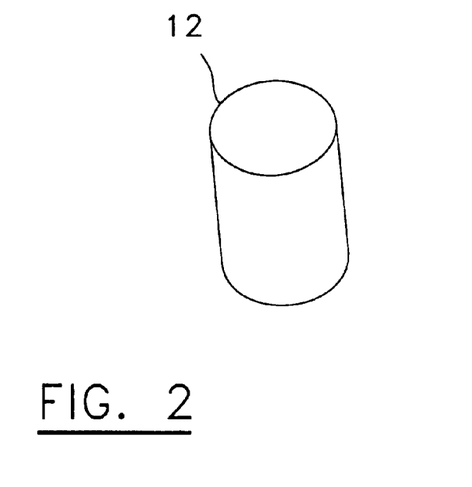
FIG. 2 is a perspective view of an ultrasonic sensor insertable in a support, according to the present invention.

Referring to FIG. 2, there is shown a conventional mono ultrasonic sensor 12 which can be used in the bracelet 14 according to the present invention. Of course, other types of sensors may also be used instead. For example, angled sensors (not shown in the Figures) can be used for detecting cracks in the pipe. The sensors can be used for volumetric measurements, or for measuring other physical features of the pipe.

Referring to FIGS. 1–8, in the case where the sensors 12 are ultrasonic sensors, each support 10 has a coupling liquid channel 16 with a bottom opening 18 extending under the sensor 12 held by the support 10.

The space between the sensor 12 and the bottom opening 18 of the support 10 is termed the "probe water chamber". In use, the probe water chamber is filled with a coupling liquid which forms a water column coupling the bottom of the sensor 12 and the surface of the pipe.

The principle for measuring the thickness of a pipe by means of ultrasounds is well known in this context. An ultrasound signal is directed toward the pipe by the ultrasonic sensor 12 through the coupling liquid in the bottom opening 18 (probe water chamber). The ultrasonic sensor 12 then picks up the echoes of the reflected ultrasound signal. The time between two echoes is measured. Since the speed of sound in the material of the pipe is known, the thickness of the pipe may be calculated. A device for calculating thickness of pipes in conjunction with the bracelet 14 according to the present invention is known under the commercial determination "TOMOSCAN" from the company RD/Tech.

In use, the ultrasonic sensor 12 is positioned at a substantially constant distance from the pipe to be inspected. The coupling liquid, such as water or a water based acoustic solution, is used to ensure a good coupling between the sensor 12 and the surface of the pipe.

The size of the bottom opening 18 of the support 10 is determined from the acoustic characteristics of the sensor 12 and the size of the pipe to be inspected. The height of the bottom opening 18 is determined such that the travel time of the ultrasound signal in the water column is longer than the travel time of the ultrasound signal in the pipe. The height of the bottom opening 18 must nevertheless be kept to a minimum to ensure that the bracelet 14 does not become too cumbersome.

In use, the base or bottom surface 54 of the support 10 is slid along the pipe to be inspected and is subject to wear because of friction. To reduce wear, the bottom surface 54 can be made of hard anodized aluminum. Other materials such as brass or plastics or stainless steel may also be used.

Figure 6:
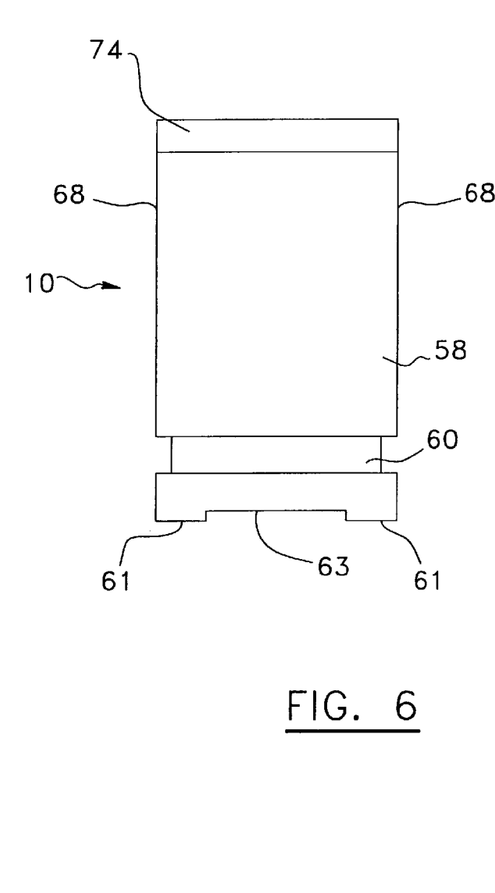
FIG. 6 is a side view of the support shown in FIG.1.

As best shown in FIG. 6, the bottom surface 54 of the support 10 may be provided with downwardly projecting skates 61 on opposite transverse portions 68 of the support 10. The bottom opening 18 of the coupling liquid channel 16 extends between the skates 61 and defines an aperture 63 between the skates 61.

In use, the skates 61 form points of contact between the support 10 and the pipe when it is slid along it. The skates 61 ensure that the support 10 is perpendicular with respect to the surface of the pipe.

Figure 3:
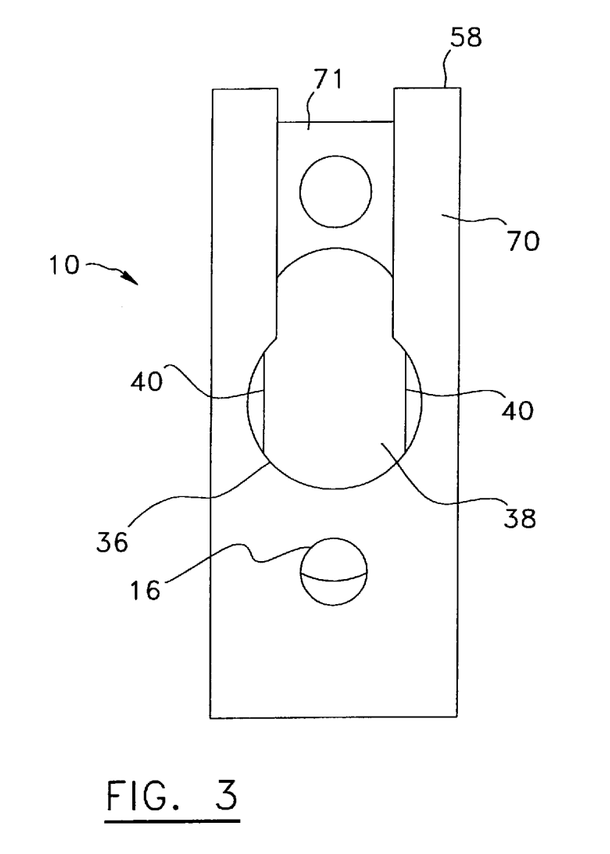
FIG. 3 is a top view of the support shown in FIG. 1.

Referring to FIGS. 1–4, each support 10 preferably has a vertical hole 36 to receive one of the sensors 12. The hole 36 has a bottom opening 38 communicating with the bottom opening 18 of the coupling liquid channel 16, as best shown in FIG. 3. The vertical hole 36 also has an abutment 40 projecting inside the hole 36 near the bottom opening 38 thereof, against which the sensor 12 comes in abutment when the sensor 12 is inserted in the hole 36.

Figure 9:
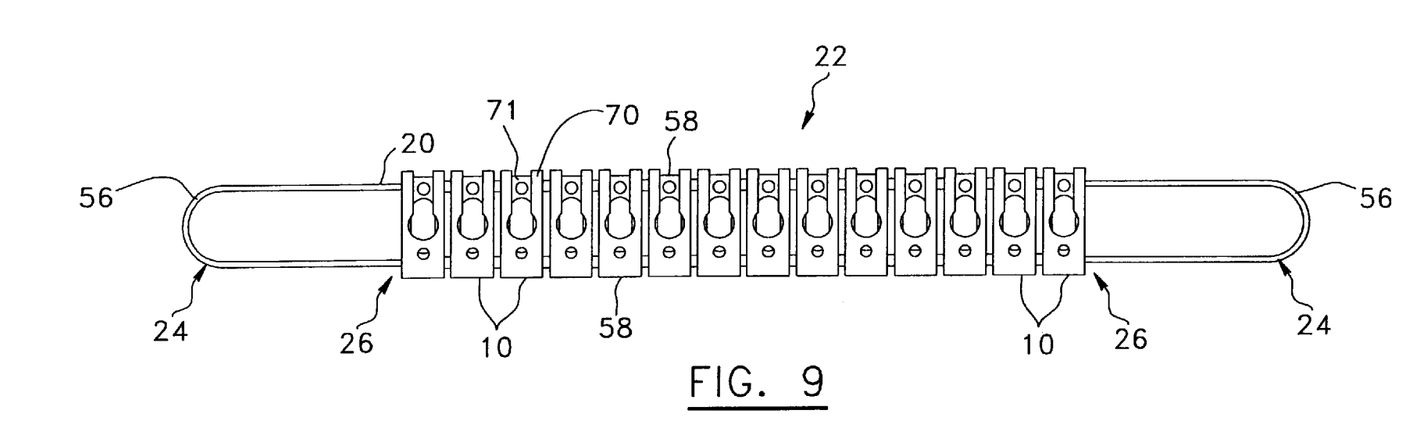
FIG. 9 is a top view of a pliant side-by-side series arrangement of supports.
Figure 10:
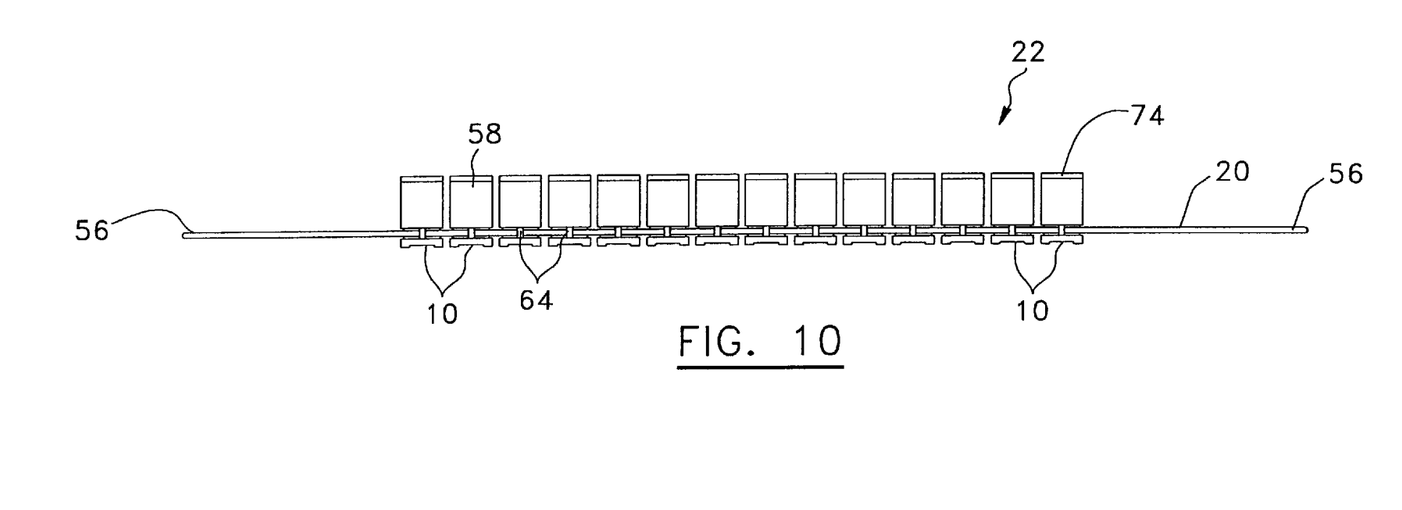
FIG. 10 is a side view of the series arrangement of supports shown in FIG. 9.

Referring to FIGS. 9 and 10, the bracelet 14 comprises a flexible attachment, which is preferably a string 20, for holding the supports 10 in a pliant side-by-side series arrangement 22. The attachment has opposite ends 24 extending beyond the supports 10 at opposite ends 26 of the series arrangement 22. The string 20 links the supports 10 to one another.

The string 20 loops back at the opposite ends 24 of the attachment and extends through opposite side portions 58 of the supports 10. The string 20 may be formed of a plastic-coated thin metal cable. The string 20 may also be made of plastic only.

Referring to FIGS. 1, 5–8 and 10, the side portions 58 of each support 10 may have lower transverse slits 60 receiving sections of the string 20. In this configuration, the side portions 58 of each support 10 may receive blocking elements operable to hold the sections of the string 20 in place inside the slits 60. The blocking elements may be formed of a set of screws 64 (see FIG. 10) inserted in holes 62 (see FIG. 4) for preventing the string 20 from slipping out of the slits 60.

Alternatively, the support 10 may have one or two through holes 66 (shown in dotted lines) instead of slits 60, for passage of the sections of the string 20 inside the support 10 on opposite transverse portions 68 of the support 10.

Referring to FIGS. 11–14, the bracelet 14 comprises a frame 28 having an inner circular opened surface 30 for installation around the pipe. The frame 28 also has a longitudinal circular side receiving surface 32 along which the series arrangement 22 of the supports 10 is mounted, as best shown in FIG. 13. The side receiving surface 32 is provided with fastening members 34 projecting at both ends 26 of the series arrangement 22 of the supports 10. The ends of the attachment 20 are supported by the fastening members 34.

The frame 28 of the bracelet 14 may have an additional longitudinal side receiving surface 72. Both side receiving surfaces 32, 72 are spaced from and face each other. The series arrangement 22 of the supports 10 then extends between the side receiving surfaces 32, 72.

Referring to FIGS. 9, 10, 11 and 13, the fastening members 34 may be formed of a pair of traverse spacing rods 34 extending between the side receiving surfaces 32, 72. The string 20 is curled about the spacing rods 34 at each end 24 of the attachment.

Figure 11:
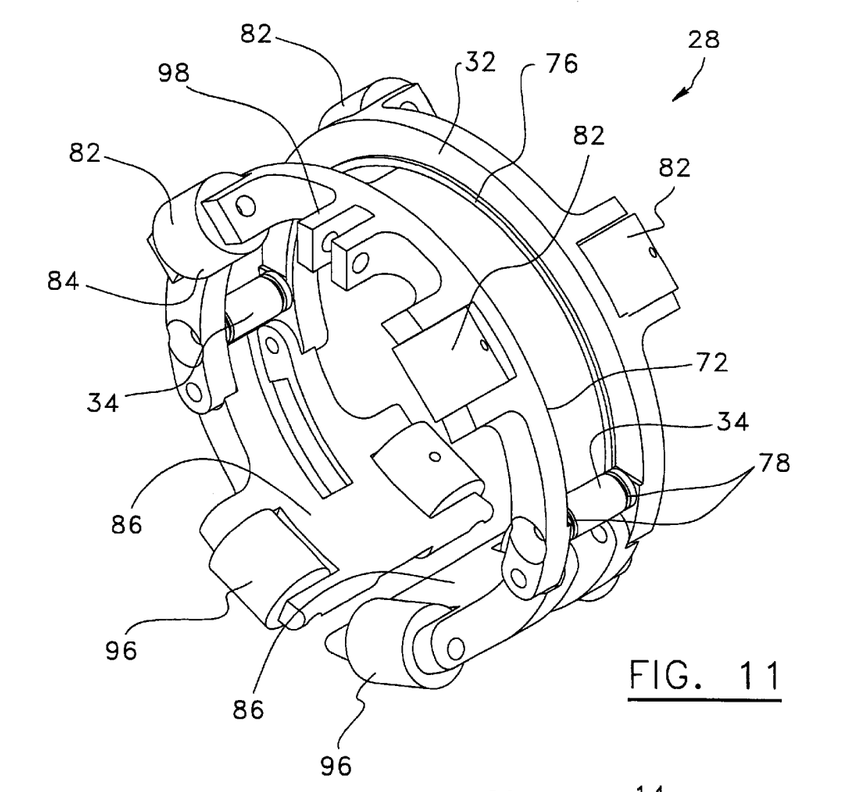
FIG. 11 is a perspective view of a frame receiving the series arrangement of supports shown in FIG. 9, according to the present invention.

Each spacing rod 34 may have peripheral guiding grooves 78 (as shown in FIG. 11) spaced from each other and guiding sections of the string 20 about the spacing rod 34.

The supports 10 may have respectively upper side projecting flanges 74, show n in FIGS. 1, 5–8 and 10. The side receiving surfaces 32, 72 may have respective lower circular projecting flanges 76 blocking passage to the flanges 74 of the supports 10, thereby preventing them from falling out of the bracelet 14.

Figure 7:
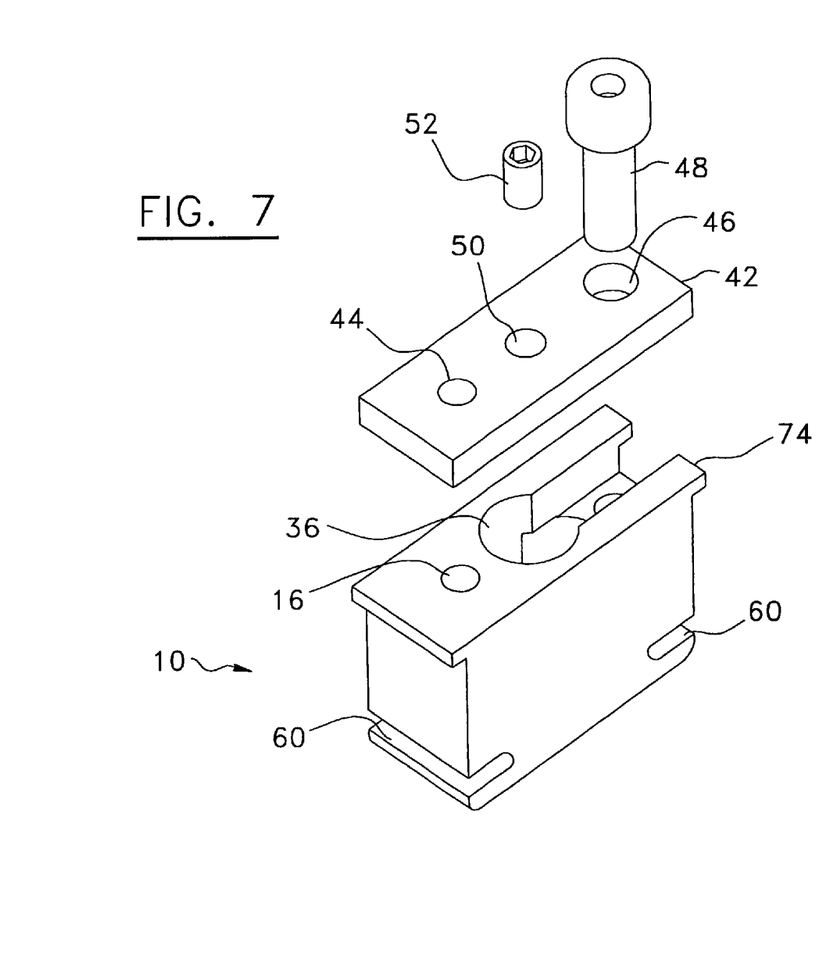
FIG. 7 is an exploded perspective view of a support with a cover, according to the present invention.
Figure 8:
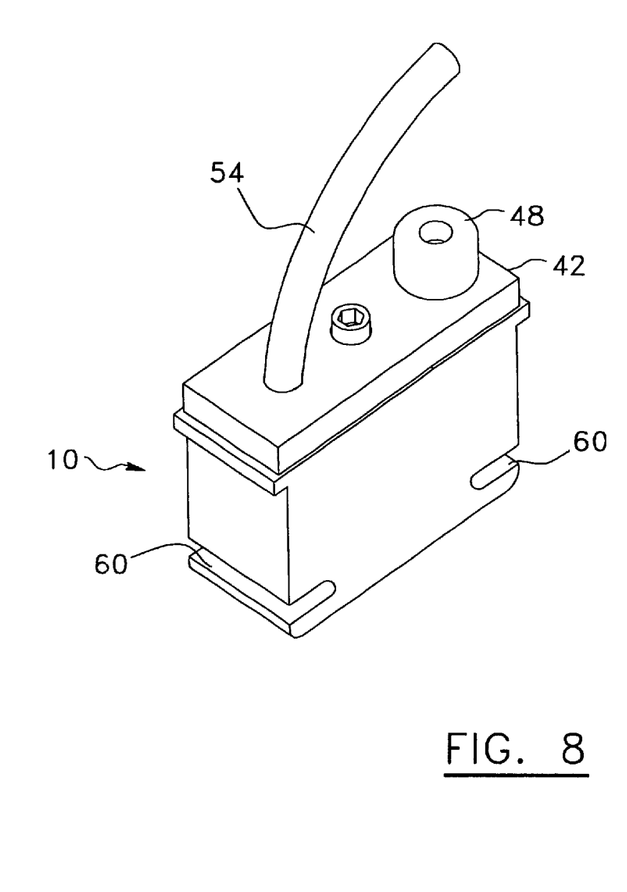
FIG. 8 is a perspective view of a support with a cover, according to the present invention.

Referring to FIGS. 7 and 8, the support 10 may be provided with a removable cover 42 extending over the hole 36. The cover 42 has a passage 44 communicating with the coupling liquid channel 16 when the cover 42 is secured to the support 10. The cover 42 has a back hole 46 receiving a screw 48 for holding the cover 42 on the support 10. The cover 42 has a middle hole 50 receiving a screw 52 also holding the cover 42 on the support 10. A tube 54 supplying the coupling liquid is inserted in the passage 44 of the cover 42.

When the bracelet 14 is moved across a non-smooth surface of a pipe, the injection of coupling liquid may cause water bubbles that distort the readings of the sensors 12. Therefore, these water bubble can be preferably eliminated through groove 71.

Figure 4:
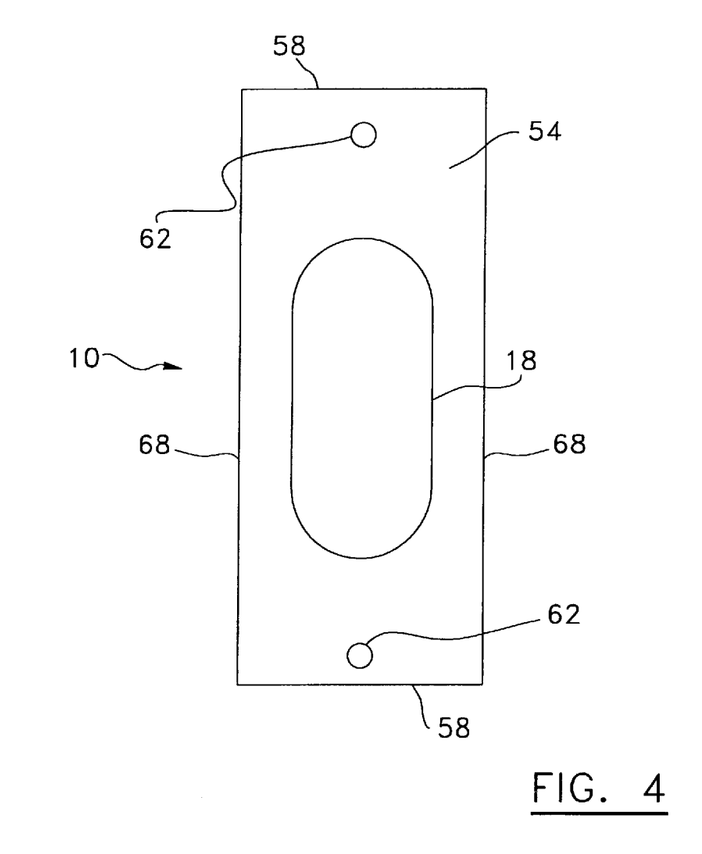
FIG. 4 is a bottom view of the support shown in FIG. 1.
Figure 5:
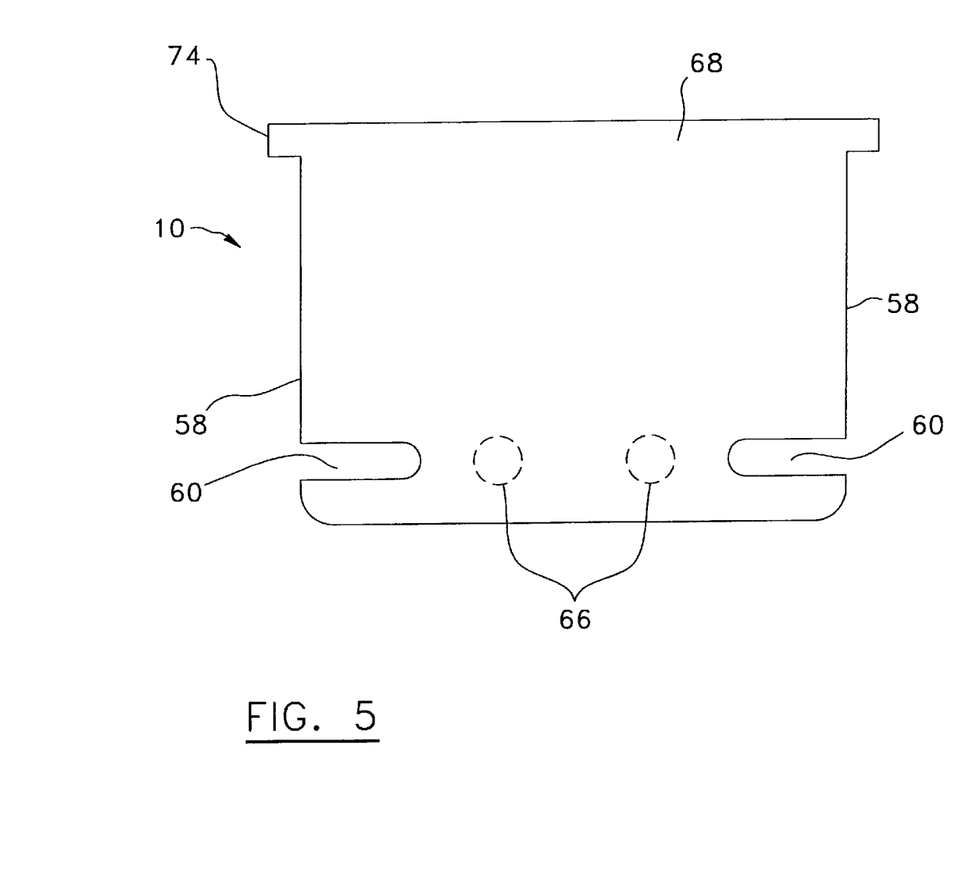
FIG. 5 is a transverse view of the support shown in FIG. 1.

Referring to FIG. 4, one way of eliminating or at least reducing water bubbles is to provide a support 10 wherein the bottom opening 18 of the coupling liquid channel 16 extends on a major portion of a bottom surface 54 of the support 10.

Figure 1:
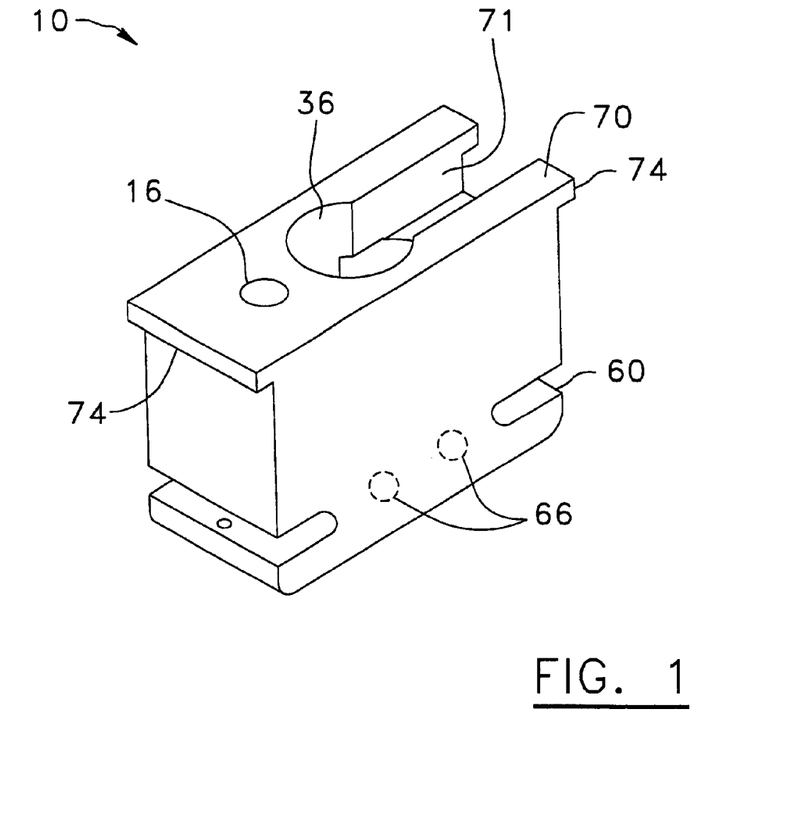
FIG. 1 is a perspective view of a support for an ultrasonic sensor, according to the present invention.

Referring to FIGS. 1, 3, and 9, each support 10 has an upper surface 70 which may be provided with a groove 71 extending from the vertical hole 36 to a side 58 of the support 10. The groove 71 communicates with the bottom opening 18 of the coupling liquid channel 16 of the support 10. These grooves 71 allow cables and tubes to be inserted therein.

Figure 12:
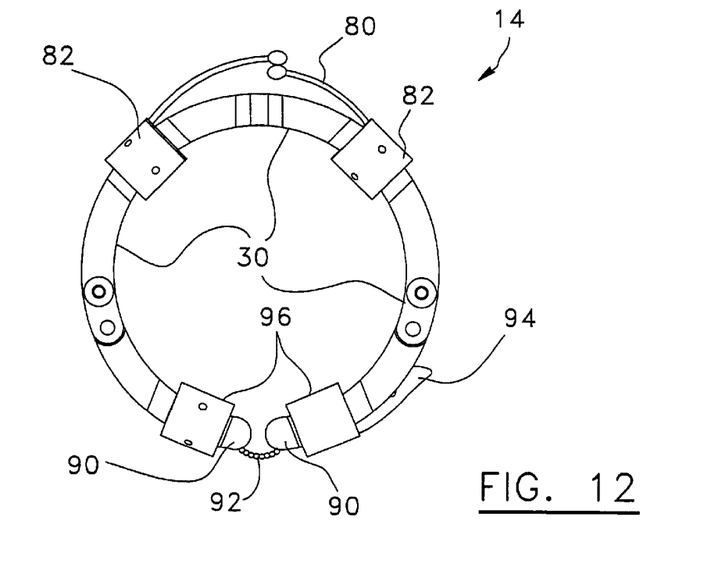
FIG. 12 is side view of a closed bracelet, according to the present invention.

Referring to FIGS. 9, 10 and 12, a detachable elastic strap 80 (as shown in FIG. 12) preferably extends over the supports 10 between the side receiving surfaces 32, 72 to tie loop portions 56 of the string 20 curled back about the spacing rods 34 and over the supports 10.

The strap 80 has the inherent property of exerting a pressure against the supports in the frame 28 so as to adapt to surface irregularities of the pipe and maintain best contact therewith. Other suitable support biasing arrangements can be used for this purpose.

Figure 14:
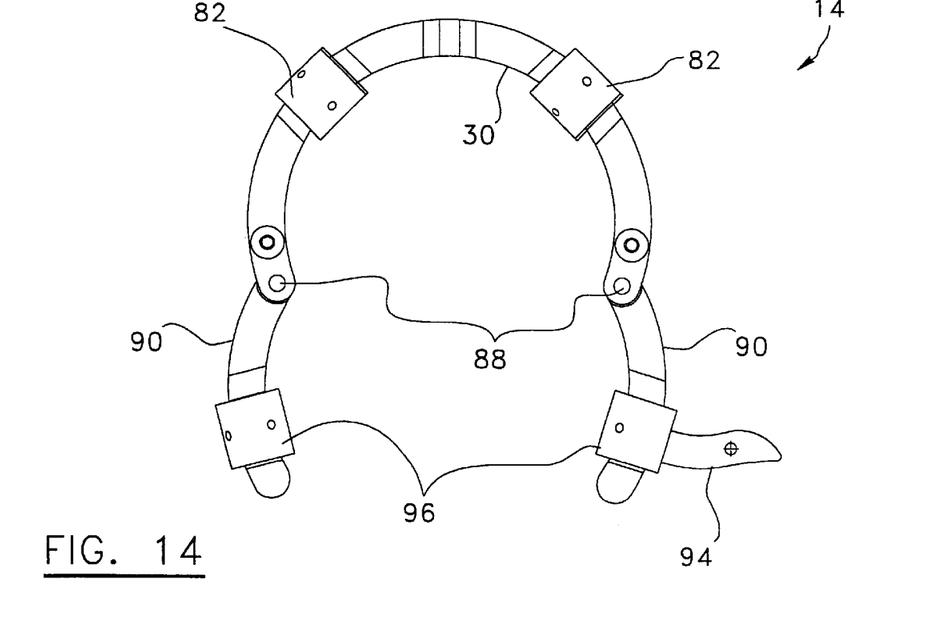
FIG. 14 is a side view of the bracelet shown in FIG. 13.

Referring to FIGS. 11 to 14, the frame 28 is preferably provided with circumferentially distributed pairs of rollers 82 extending behind the side receiving surfaces 32, 72 and having rolling surfaces 84 projecting past the inner circular opened surface 30 as best shown in FIG. 14, for displacement of the bracelet 14 along the pipe.

The bracelet 14 preferably further has an openable clasp 86 extending between open ends 88 of the frame 28, for closing the bracelet 14 around the pipe.

The clasp 86 may be formed of a pair of legs 90 pivotally connected respectively to the open ends 88 of the frame 28, forming complementary extensions thereof. The clasp 86 also has a fastener for fastening the legs 90 with each other.

As shown in FIG. 12, the fastener may be a spring 92 having an end fastened to one of the legs 90 and an opposite end fastened to a tightening lever 94 mounted on the other leg 90 and operable to selectively pull and release the spring 92.

The legs 90 may also have a pair of rollers 96 extending substantially at complementary positions to the pairs of rollers 82 on the frame 28.

Referring to FIG. 11, the frame 28 is preferably provided with a position encoder mounting bracket 98 projecting behind the side receiving surface 72, for receiving a position encoder (not shown) which measures the displacement of the bracelet 14 along the pipe.

In experimental tests, the bracelet was successfully used to inspect pipes of 2 and 2.5 inches in diameter and within a 145 degrees arc. The supports 10 maintain a perpendicular position with respect to the surface of the pipe (even if the pipe is bent, or has an elbow, or has an oval surface), which provides more accurate readings.

The bracelet 14 may be provided with an extensible slidable frame (not shown) which is adaptable and adjustable to different pipe diameters. The bracelet is then adjustably mounted on each of those pipes.

One of the advantages of the bracelet is that it is easily installed and uninstalled around the pipes of nuclear reactors. Thereby, as measurements are taken quickly and accurately, the operator of the bracelet is less exposed to harmful radiation.

To minimize the exposure to radiation, the bracelet may be provided with a motorized mechanism controlled from a remote location (not shown). The motorized mechanism moves the bracelet along the pipe.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A bracelet for moving sensors along a pipe, comprising:
   a number of side-by-side positionable supports for removably holding the sensors respectively;
   a flexible attachment means for holding all the supports in a pliant side-by-side series arrangement around the pipe, the attachment means having opposite ends extending beyond the supports at opposite ends of the series arrangement; and
   a frame having an inner circular opened surface for installation around the pipe, and a longitudinal circular side receiving surface along which the series arrangement of the supports is mounted, the side receiving surface being provided with fastening members projecting at both ends of the series arrangement of the supports, the ends of the attachment means being supported by the fastening members.

2. The bracelet according to claim 1, wherein each support has a coupling liquid channel with a bottom opening extending under the sensor held by the support.

3. The bracelet according to claim 2, wherein each support comprises:
   a vertical hole to receive one of the sensors, the hole having a bottom opening communicating with the bottom opening of the coupling liquid channel, and an abutment projecting inside the hole near the bottom opening thereof, against which said one of the sensors comes in abutment when said one of the sensors is inserted in the hole.

4. The bracelet according to claim 3, wherein each support is provided with a removable cover extending over the hole, the cover having a passage communicating with the coupling liquid channel.

5. The bracelet according to claim 4, wherein the bottom opening of the coupling liquid channel of each support extends on a major portion of a bottom surface thereof.

6. The bracelet according to claim 5, wherein each support has an upper surface provided with a groove extending from the vertical hole to a side of the support, the groove communicating with the bottom opening of the coupling liquid channel of the support.

7. The bracelet according to claim 2, wherein each support has a bottom surface provided with downwardly projecting skates on opposite transverse portions of the support, the bottom opening of the coupling liquid channel extending between the skates.

8. The bracelet according to claim 7, wherein each support comprises:
   a vertical hole to receive one of the sensors, the hole having a bottom opening communicating with the bottom opening of the coupling liquid channel, and an abutment projecting inside the hole near the bottom opening thereof, against which said one of the sensors comes in abutment when said one of the sensors is inserted in the hole.

9. The bracelet according to claim 7, wherein the flexible attachment means comprises a string linking the supports to one another.

10. The bracelet according to claim 7, wherein the skates of each support are made of hard anodized aluminum.

11. The bracelet according to claim 7, wherein the frame has an additional longitudinal side receiving surface, both side receiving surfaces being spaced from and facing each other, the series arrangement of the supports extending between the side receiving surfaces.

12. The bracelet according to claim 1, wherein the flexible attachment means comprises a string linking the support to one another.

13. The bracelet according to claim 12, wherein the string loops back at the opposite ends of the attachment means and extends through opposite side portions of the supports.

14. The bracelet according to claim 13, wherein the side portions of each support has lower transverse slits receiving sections of the string, and blocking elements operable to hold the sections of the string in place inside the slits.

15. The bracelet according to claim 12, wherein the string is formed of a plastic-coated thin metal cable.

16. The bracelet according to claim 12, wherein each support has a traverse through hole receiving a section of the string.

17. The bracelet according to claim 16, wherein each support has an additional traverse through hole receiving an additional section of the string, the through holes being spaced from each other and extending through opposite side portions of the support.

18. The bracelet according to claim 1, wherein each support has a bottom surface made of hard anodized aluminum.

19. The bracelet according to claim 1, wherein the frame has an additional longitudinal side receiving surface, both side receiving surfaces being spaced from and facing each other, the series arrangement of the supports extending between the side receiving surfaces.

20. The bracelet according to claim 19, wherein the supports have respectively upper side projecting flanges, and the side receiving surfaces have respectively lower circular projecting flanges blocking passage to the flanges of the supports.

21. The bracelet according to claim 19, wherein flexible attachment means comprises a string linking the supports to one another, the string looping back at the opposite ends of the attachment means and extending through opposite side portions of the supports.

22. The bracelet according to claim 21, wherein the fastening members comprise a pair of traverse spacing rods extending between the side receiving surfaces, the string being curled about the spacing rods at each end of the attachment means.

23. The bracelet according to claim 22, wherein each spacing rod has peripheral guiding grooves spaced from each other and guiding sections of the string about the spacing rod.

24. The bracelet according to claim 22, further comprising a detachable elastic strap extending over the supports between the side receiving surfaces and tying loop portions of the string curled back about the spacing rods and over the supports.

25. The bracelet according to claim 19, wherein the frame comprises circumferentially distributed pairs of rollers extending behind the side receiving surfaces and having rolling surfaces projecting past the inner circular opened surface, for displacement of the bracelet along the pipe.

26. The bracelet according to claim 1, further comprising an openable clasp extending between open ends of the frame, for losing the bracelet around the pipe.

27. The bracelet according to claim 26, wherein the clasp comprises:
   a pair of legs pivotally connected respectively to the open ends of the frame, and forming complementary extensions thereof; and
   a fastening means for fastening the legs with each other.

28. The bracelet according to claim 27, wherein the fastening means comprises a spring having an end fastened to one of the legs and an opposite end fastened to a tightening lever mounted on the other leg and operable to selectively pull and release the spring.

29. The bracelet according to claim 27, wherein the legs comprise pairs of rollers extending substantially at complementary positions to pairs of rollers provided on the frame.

30. The bracelet according to claim 1, wherein the frame has a position encoder mounting bracket projecting behind the side receiving surface.

31. The bracelet according to claim 1, further comprising a detachable elastic strap mounted onto the frame and extending over the supports for pushing the supports against the pipe.

32. The bracelet according to claim 31, wherein each support has a coupling liquid channel with a bottom opening extending under the sensor held by the support.

33. The bracelet according to claim 32, wherein each support has a bottom surface provided with downwardly projecting skates on opposite transverse portions of the support, the bottom opening of the coupling liquid channel extending between the skates.

34. The bracelet according to claim 33, wherein the frame has an additional longitudinal side receiving surface, both side receiving surfaces being spaced from and facing each other, the series arrangement of the supports extending between the side receiving surfaces.

35. The bracelet according to claim 34, wherein the frame comprises circumferentially distributed pairs of rollers extending behind the side receiving surfaces and having rolling surfaces projecting past the inner circular opened surface, for displacement of the bracelet along the pipe.

36. The bracelet according to claim 32, wherein the frame has an additional longitudinal side receiving surface, both side receiving surfaces being spaced from and facing each other, the series arrangement of the supports extending between the side receiving surfaces.

37. The bracelet according to claim 36, wherein the frame comprises circumferentially distributed pairs of rollers extending behind the side receiving surfaces and having rolling surfaces projecting past the inner circular opened surface, for displacement of the bracelet along the pipe.

38. The bracelet according to claim 32, wherein the supports have respectively upper side projecting flanges, and the side receiving surfaces have respectively lower circular projecting flanges blocking passage to the flanges of the supports.

39. The bracelet according to claim 32, wherein the flexible attachment means comprises a string linking the supports to one another.

40. The bracelet according to claim 32, further comprising an openable clasp extending between open ends of the frame, for closing the bracelet around the pipe.

41. The bracelet according to claim 40, wherein the clasp comprises:

a pair of legs pivotally connected respectively to the open ends of the frame, and forming complementary extensions thereof; and a fastening means for fastening the legs with each other.

42. The bracelet according to claim 41, wherein the legs comprise pairs of rollers extending substantially at complementary positions to pairs of rollers provided on the frame.

43. The bracelet according to claim 40, wherein the fastening means comprises a spring having an end fastened to one of the legs and an opposite end fastened to a tightening lever mounted on the other leg and operable to selectively pull and release the spring.

* * * * *